US00PP12149P2

(12) United States Plant Patent
Rother

(10) Patent No.: US PP12,149 P2
(45) Date of Patent: Oct. 16, 2001

(54) OSTEOSPERMUM PLANT NAMED 'VANILLA CREAM'

(76) Inventor: Reinhard W. Rother, P.B. 327, Emerald, Victoria (AU)

( * ) Notice: Subject to any disclaimer, the term of this patent is extended or adjusted under 35 U.S.C. 154(b) by 0 days.

(21) Appl. No.: 09/545,911

(22) Filed: Apr. 9, 2000

(51) Int. Cl.[7] ..... A01H 5/00
(52) U.S. Cl. ..... Plt./360

(58) Field of Search ..... Plt./360

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Osteospermum plant named 'Vanilla Cream', characterized by its compact, mounding and outwardly spreading growth habit; dark green leaves; freely branching habit; ivory-colored ray florets; numerous inflorescences per lateral stem; long flowering period; and relative tolerance to high temperatures.

1 Drawing Sheet

BACKGROUND OF THE INVENTION

The present Invention relates to a new and distinct cultivar of Osteospermum plant, botanically known as *Osterspermum ecklonis,* and referred to by the cultivar name Vanilla Cream.

The new cultivar is a product of a planned breeding program conducted by the Inventor in Emerald, Victoria, Australia. The objective of the breeding program was to create new compact Osteospermum cultivars with large inflorescences and tolerance to high temperatures.

The new cultivar originated from a cross made by the Inventor of a proprietary selection of *Osteospermum ecklonis* identified as code number ivory 41 as the female, or seed, parent and a proprietary selection of *Osteospermum ecklonis* identified as code number ivory 96, as the male, or pollen, parent. The new Osteospermum was selected by the Inventor as a flowering plant within the progeny of this cross in a controlled environment in Emerald, Victoria, Australia in 1994.

Plants of the new cultivar are different from plants of the female parent, the selection ivory 41 in plant habit and inflorescence size. Plants of the new Osteospermum are less trailing and have more rounded ray florets than plants of the male parent, the selection ivory 96.

Asexual propagation of the new cultivar by terminal cuttings at Emerald, Victoria, Australia, has shown that the unique features of this new Osteospermum are stable and reproduced true to type in successive generations.

SUMMERY OF THE INVENTION

The following traits have been repeatedly observed and are determined to be the unique characteristics of 'Vanilla Cream'. These characteristics in combination distinguish 'Vanilla Cream' as a new and distinct cultivar:

1. Compact, mounding and outwardly spreading growth habit.

2. Dark green leaves.

3. Freely branching habit.

4. Ivory-colored ray florets.

5. Numerous inflorescences per lateral stem.

6. Long flowering period.

7. Relatively tolerant to high temperatures.

The new cultivar can be compared to the Osteospermum cultivar Cream Symphony, not patented. However in side-by-side comparisons conducted in Emerald, Victoria, Australia, plants of the new cultivar are more outwardly spreading, are larger and stronger, have ray florets with yellow-striped lower surfaces and have more florets per inflorescence than plants of the cultivar Cream Symphony.

The cultivar Vanilla Cream has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Osteospermum.

The photograph at the top of the sheet comprises a side perspective view of a typical flowering plant of 'Vanilla Cream'.

The photograph at the bottom of the sheet is a close-up view of an inflorescence bud, lower surface of typical ray florets, typical inflorescence and upper and lower surfaces of typical leaves of 'Vanilla Cream'. The age and the environmental conditions of the plant depicted in the photograph are the same as those described in the Detailed Botanical Description.

DETAILED BOTANICAL DESCRIPTION

The following observations, measurements and values describe 20-cm containers with three 10 week old plants of the new cultivar grown in Bonsall, Calif., under outdoor, full-sun conditions with dry temperatures ranging from 21 to 35° C. and night temperatures ranging from 13 to 18° C.

Color references are made to The Royal Horticultural Society Colour Chart except where general terms of ordinary dictionary significance are used.

Botanical classification: *Osteospermum ecklonis* cultivar Vanilla Cream.

Parentage:

*Female, or seed, parent.*—Proprietary selection of *Osteospermum ecklonis* identified as code number ivory 41.

*Male, or pollen, parent.*—Proprietary selection of *Osteospermum ecklonis* identified as code number ivory 96.

Propagation:

*Type.*—By terminal cuttings and by tissue culture.

*Time to initiate roots.*—About 12 to 18 days at 22° C.

*Rooting habit.*—Fibrous, thick and fleshy.

Plant description:

*Appearance.*—Perennial herbaceous container and garden plant. Very broad inverted triangle. Compact, mounding and outwardly spreading growth habit; somewhat open plant habit. Dark green foliage. Inflorescences held above and beyond the foliage on moderately strong peduncles. Freely branching with about 10 lateal branches; removal of terminal apices (pinching) will enhance branching.

*Crop time.*—About 8 to 10 weeks are required to produce a finished, flowering plant in a 10-cm container.

*Vigor.*—Moderately vigorous.

*Plant height.*—About 28 cm.

*Plant spread.*—About 39 cm.

*Lateral branch description.*—Length: About 19 cm. Diameter: About 5 mm. Internode length: About 1.2 cm. Texture: Glabrous; stems thick and somewhat succulent. Color: 144B.

*Foliage description.*—Leaves alternate, single. Quantity of leaves per lateral branch: About 22. Length, fully expanded leaves, basal: About 6.8 cm. Width, fully expanded leaves, basal: About 3 cm. Shape. Elliptic. Apex: Broadly acute. Base: Attenuate, sessile. Margin: Entire with irregularly-spaced teeth. Aspect: undulate; twisted. Texture: Leathery and tough; smooth, glabrous; thick cuticle. Color: Young foliage, upper surface: 147A. Young foliage, lower surface: 147B. Fully expanded foliage, upper surface: 137A. Fully expanded foliage, lower surface: 137B. Attenuated leaf base: 144A to 144B. Venation, upper surface: 137A. Venation, under surface: 137B.

Inflorescence description:

*Appearance/longevity.*—Daisy-type composite inflorescence form. Inflorescences displayed above and beyond foliage on moderately strong peduncles arising from leaf axils. Disc and ray florets arranged acropetally on a capitulum. Typically about five buds and opened inflorescences per lateral stem. Inflorescences last about one week on the plant. New inflorescences bypass older inflorescences. Inflorescences persistent.

*Flowering response.*—Plants flower continuously from April to October in the Northern Hemisphere.

*Fragrance.*—None detected.

*Inflorescence size.*—Diameter: About 6.5 cm. Depth (height): About 1.5 cm. Diameter of disc: About 1.2 cm.

*Inflorescence buds.*—Length: About 1.5 cm. Width: About 1 cm. Shape: Pointed ovoid. Color: 1B.

*Ray florets.*—Quantity of ray florets per inflorescence: About 24 in a single whorl. Length: About 3.3 cm. Width: About 8 mm. Shape: Ligulate. Apex: Broadly acute; minute tri-dentate. Base: Attenuate; acute. Margin: Entire. Aspect: Slightly tilted upright to horizontal. Texture: Smooth, satiny. Color: When opening, upper surface: 155A. When opening, lower surface: Longitudinal stripes, 6D. Fully opened, upper surface: 155A to 155C. Fully opened, under surface: Longitudinal stripes, 6D.

*Disc florets.*—Quantity of disc florets per inflorescence: Numerous, about 120. Shape: Tubular; five-lobed, fluted at apex. Length: About 8 mm. Width: About 2 mm. Color: Immature: 156A to 156B. Mature: 157B.

*Phyllaries.*—Quantity per inflorescence and arrangement: About 26 per inflorescence; double whorl, fused at base. Length: About 1 cm. Shape: Narrowly ligulate. Apex: Sharply acute. Margin: Entire; edges, membranous. Texture: Smooth. Color: Upper surface: 137C. Lower surface: 137A.

*Peduncle.*—Length: First peduncle: About 9 cm. Fourth peduncle: About 8 cm. Aspect: Moderately strong, inflorescences held erect to about 40 to 45° to the vertical axis of the plant above and beyond the foliage. Texture: Slightly coarse. Color: 143A.

*Reproductive organs.*—Androecium: Present on disc florets only. Stamens: Five, fused. Anther shape: Elongated. Anther size: About 3 mm. Anther color: 161A. Pollen: Scarce. Pollen color: 12A. Gynoecium: Present on ray and disc florets. Pistils: One per floret. Pistil Length: About 7 mm. Stigma shape: Bipartite. Stigma color: 155A. Style length: About 5 mm. Style color: 155A. Ovary color: 149C.

*Seed.*—Seed production has not been observed to date.

Disease resistance: Resistance to pathogens common to Osteospermum has not been observed on plants of the new Osteospermum.

High temperature tolerance: Plants of the new Osteospermum have been observed to be relatively tolerant to high temperatures.

It is claimed:

1. A new and distinct cultivar of Osteospermum plant named 'Vanilla Cream', as illustrated and described.

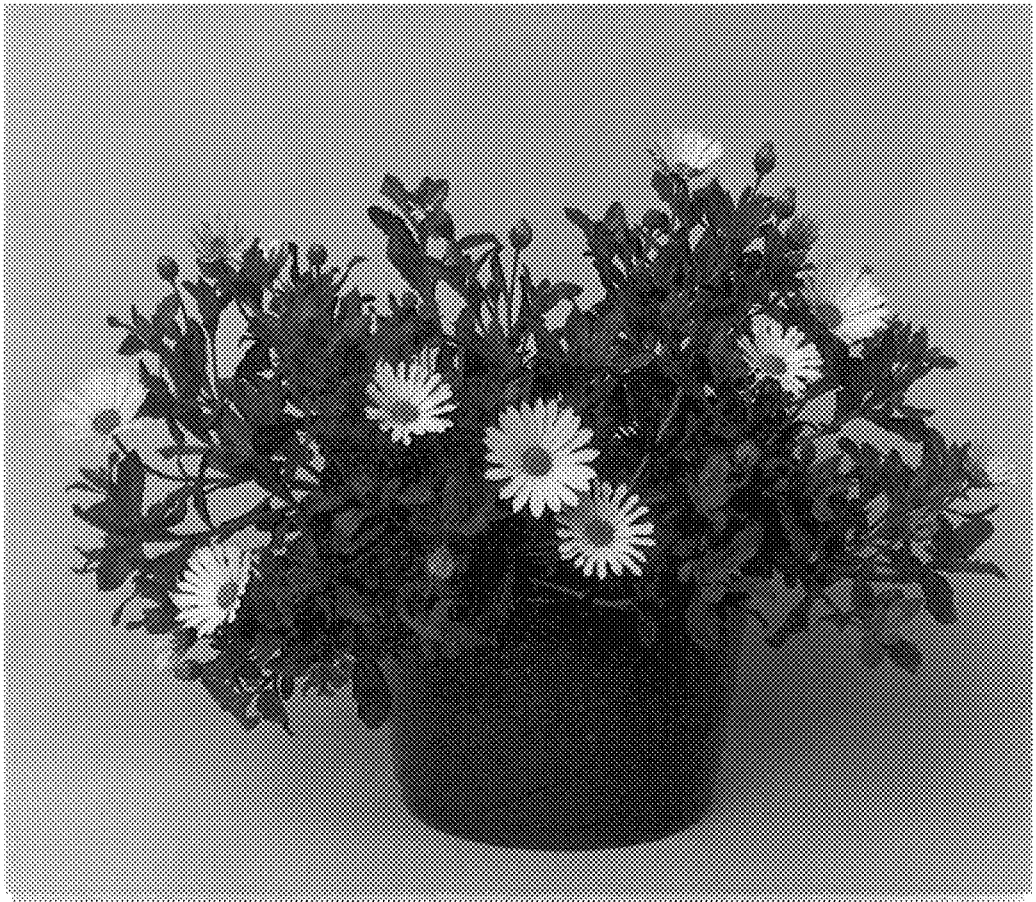
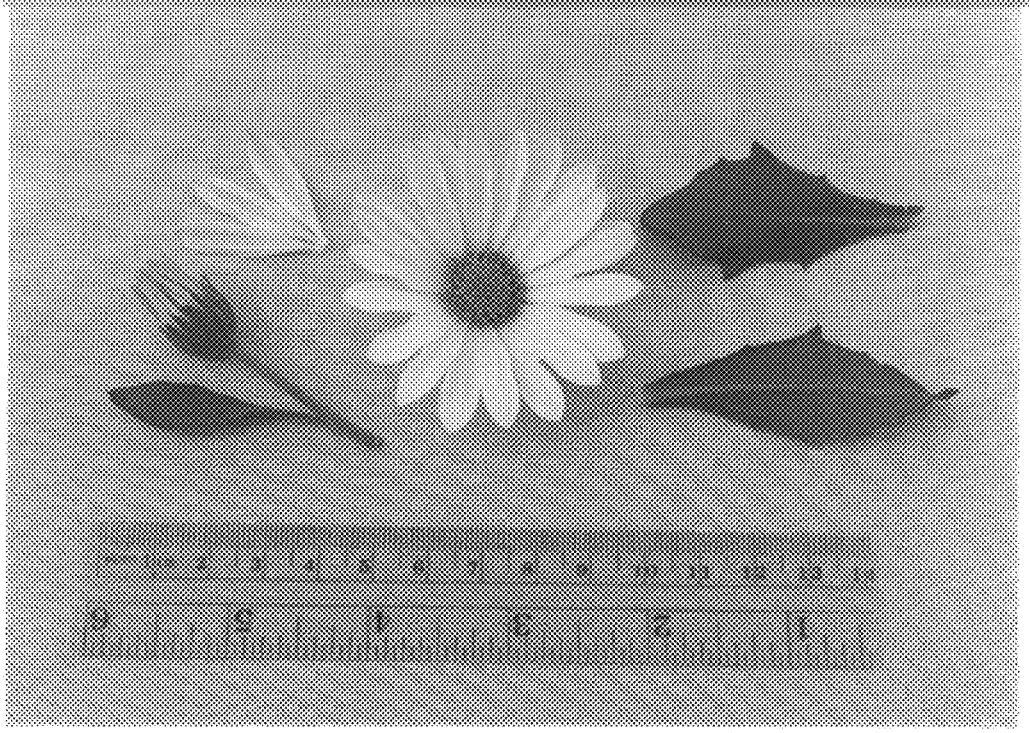

* * * * *